(12) United States Patent
Guez et al.

(10) Patent No.: US 10,856,803 B1
(45) Date of Patent: Dec. 8, 2020

(54) METHOD AND APPARATUS FOR CLOSED-LOOP BRAIN STIMULATION

(71) Applicant: Aqeel LLC, Dover, DE (US)

(72) Inventors: Allon Guez, Narberth, PA (US); Bruce Katz, Philadelphia, PA (US); Jon Guez, Philadelphia, PA (US)

(73) Assignee: Aqeel, LLC, Dover, DE (US)

( * ) Notice: Subject to any disclaimer, the term of this patent is extended or adjusted under 35 U.S.C. 154(b) by 191 days.

(21) Appl. No.: 16/106,032

(22) Filed: Aug. 21, 2018

Related U.S. Application Data

(60) Provisional application No. 62/548,265, filed on Aug. 21, 2017.

(51) Int. Cl.
*A61B 5/00* (2006.01)
*A61B 5/16* (2006.01)
*A61B 5/048* (2006.01)
*A61N 1/36* (2006.01)
*G16H 40/63* (2018.01)
*A61N 1/02* (2006.01)
*G16H 20/30* (2018.01)

(52) U.S. Cl.
CPC ............ *A61B 5/4836* (2013.01); *A61B 5/048* (2013.01); *A61B 5/165* (2013.01); *A61B 5/168* (2013.01); *A61N 1/025* (2013.01); *A61N 1/36025* (2013.01); *A61N 1/36031* (2017.08); *G16H 20/30* (2018.01); *G16H 40/63* (2018.01)

(58) Field of Classification Search
CPC ....... A61B 5/4836; A61B 5/048; A61B 5/165; A61N 1/025; A61N 1/36025; A61N 1/36031
USPC .......................................................... 607/45
See application file for complete search history.

(56) References Cited

U.S. PATENT DOCUMENTS

| | | | |
|---|---|---|---|
| 4,919,143 A | 4/1990 | Ayers | |
| 6,488,617 B1 | 12/2002 | Katz | |
| 2007/0142874 A1* | 6/2007 | John | A61N 2/006 607/45 |
| 2008/0319505 A1 | 12/2008 | Boyden et al. | |
| 2015/0066104 A1* | 3/2015 | Wingeier | A61N 1/08 607/45 |

FOREIGN PATENT DOCUMENTS

WO WO2018/067761 4/2018

\* cited by examiner

*Primary Examiner* — Amanda K Hulbert
*Assistant Examiner* — Philip C Edwards
(74) *Attorney, Agent, or Firm* — Joseph E. Maenner; Maenner & Associates, LLC

(57) ABSTRACT

A closed loop brain stimulation system includes a means for reading electrophysiological signals from the brain; means for reading other biometric signals; means for stimulating the brain; and a control algorithm that dynamically adjusts the parameters of stimulation to minimize a reference utility function that computes the difference between the current and desired brain states, and current and desired biometric states.

18 Claims, 10 Drawing Sheets

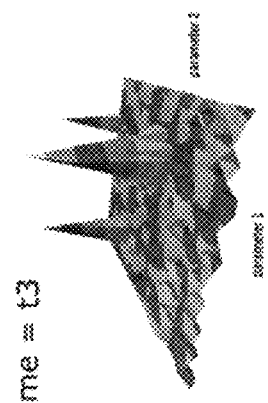
FIG. 3
FIG. 3A  FIG. 3B  FIG. 3C

METHOD AND APPARATUS FOR CLOSED-LOOP BRAIN STIMULATION

CROSS-REFERENCE TO RELATED APPLICATION

The present application claims priority from U.S. Provisional Patent Application Ser. No. 62/548,265, filed on Aug. 21, 2018, which is incorporated herein by reference in its entirety.

BACKGROUND OF THE INVENTION

Technical Field

The present disclosure relates generally to methods, systems, and apparatuses, for the creation of a closed-loop brain stimulation system. Such a system can be used, inter alia, for the alleviation of brain-based pathologies such major depressive disorder (MDD) and associated affective disorders, epilepsy, Parkinson's, ADHD, and other mental illnesses including bipolar and schizoid-related diseases. It can also be applied to enhancing non-pathological brain functioning including but not limited to cognitive enhancement in general and problem-solving in particular, creativity enhancement, the enhancement and fine-tuning of motor skills, perceptual tasks such as pattern recognition in a noisy environment, and a number of "soft" skills such as social engagement, emotional intelligence, and the like.

In the following, stimulation refers to a technique of altering the state of the brain by a targeted addition of electrical or mechanical energy. In the primary embodiment of this document, this stimulation is in the form of transcranial electrical stimulation (TES), but other non-invasive stimulation techniques may leverage the proposed loop methodology including transcranial magnetic stimulation (TMS), and acoustic stimulation, and invasive stimulation techniques such as deep brain stimulation (DBS), or a to be developed stimulation technique.

In the following, brain reading (alternatively, brain imaging) refers to an apparatus that obtains information about the activity of the brain as opposed to its fixed structure. In the primary embodiment, this is carried out via the amplification of the small currents that the brain generates on the surface of the scalp (EEG), but can include function magnetic resonance imaging (fMRI), function near-infrared spectroscopy (fNIRS), magnetoencephalography (MES), or a to be developed brain reading technique.

In the following, biometric data refers to any unfiltered or computed data gathered by wearables and other detectors. Such data may include "raw" biometric signals such as galvanic skin response, heart rate, breathing rate, temperature etc. but also computed fields derives from one or more raw signals such as sleep quality, step count per unit time, balance, etc.

In the following, a biomarker refers to a local or global brain state. If local, the marker will be computed within a fixed region or significant physiological substructure, and if global, over the entire brain itself. Such markers may be intrinsic or relative, with the former measuring the state within the region, and the latter indicative of the interaction between one or more regions. Biomarkers in general will be either correlated or causally related to a given mental state, and if the latter, an influence on the biomarker will of necessity also influence this mental state.

An open loop brain stimulation system is a system that attempts to alter a biomarker with the intention of also influencing the associated mental state. It determines the biomarker to influence and the stimulation method based on a priori principles, and crucially, does not assess the effect of the stimulation in real time. As an example, TMS for MDD applies a rapid rate signal above the left prefrontal cortex. The justification for this procedure is twofold: rapid TMS produces an excitatory effect on the brain, and the left prefrontal cortex typically shows a deficit of activity in MDD. However, at no point in this process is the effect of the stimulation measured, either directly on the brain, or through other indirect biometric signals.

A closed loop stimulation system, in contrast, continuously monitors the brain and optionally other biometric signals, during or after the stimulation period, and adjusts the parameters of the stimulation in order to optimally influence the given biomarker. For example, in the case of TMS for MDD, activity in the left prefrontal cortex could be monitored by EEG or other means. The rate of stimulation could then be adjusted to maximize the effect of this stimulation; other parameters such as the placement of the TMS magnet could also be altered.

In general, a multivariate set of parameters can be manipulated to optimize the effect on the given biomarker. In order to carry out this optimization, a control algorithm is interposed between the read signals from the brain, or other biometric indicators, and the stimulation device. The task of the control algorithm is to assess the effect of perturbing the multiple stimulation parameters, singly, or in groups, and adjust them to maximally influence the given biomarker in the desired direction.

Thus, the general sequence of operations in closed loop system are as follows: an initial stimulus is either chosen at random, or derived from first principles as in open loop stimulation. This stimulus is applied to brain. Then a reading from the brain is taken, and this combined with optional biometric signals. These signals are fed into the control algorithm, which decides on the next round of stimulation. This loop continues as long as desired. In a clinical setting, this will generally be limited to less than one half hour, although more portable embodiments that allow longer periods of stimulation are possible.

The proposed advantages of this type of closed loop system relative to the open loop brain stimulation methodology include the following: a) the ability to take into account individual differences in brain anatomy and physiology without the need for initial complex measurements, b) the ability to adjust to changing brain dynamics in real time to optimize a desired biomarker, c) the ability to integrate seamlessly external sources of information such as biometric data into the function that will be optimized, d) the ability to explore complex electrode montages of stimulation each with multiple stimulation parameters, e) all of the above operating in consort to more efficacious therapeutic delivery system than the corresponding open loop counterpart.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention is a closed loop brain stimulation system, comprising means for reading electrophysiological signals from the brain; means for reading other biometric signals; means for stimulating the brain;

and a control algorithm that dynamically adjusts the parameters of stimulation to minimize a reference utility function that computes the difference between the current and desired brain states, and current and desired biometric states.

In another embodiment, the present invention provides a method of dynamically constructing an individualized biomarker comprising the steps of: obtaining data sets of performance statistics and associated brain states; applying a machine-learning algorithm to these data sets to produce a model; and using the model as a means of determining the value of a biomarker in the context of a utility function.

We propose that closed loop brain stimulation will be more efficacious in the treatment of various brain pathologies as well as enhancement of existing non-pathological function of the brain than its open loop counterpart.

Open loop stimulation is limited to an initial a priori determination of the best form of stimulation. In contrast, closed loop stimulation continuously adjusts the stimulation regime on the basis of feedback from either the brain or the body or both.

The closed loop methodology applies to a number of embodiments both with respect to differing stimulation/imaging combinations, and with respect to pathological treatment and non-pathological enhancement. We propose, however, that the underlying technological glue linking these embodiments is the control algorithm that operates in this multiple input multiple output (MIMO) to determine the optimal stimulation regime.

We further propose that the combined system comprising inputs from brain imaging devices and from biometrics, the control algorithm, and the stimulation of possibly complex electrode montages or multiple points of stimulation, in its original embodiment or in an optional portable embodiment, will extend brain stimulation to new previously unexplored areas of application both for treatment of brain-based disorders and enhancement of skills that are currently suboptimal.

BRIEF DESCRIPTION OF THE DRAWINGS

The foregoing and other aspects of the present invention are best understood from the following detailed description when read in connection with the accompanying drawings. For the purpose of illustrating the invention, there are shown in the drawings embodiments that are presently preferred, it being understood, however, that the invention is not limited to the specific instrumentalities disclosed. Included in the drawings are the following Figures:

FIG. 3 shows the utility function (inverted) as a function of a single stimulation parameter.

FIG. 3A shows the utility function (inverted) as a dynamic function of two stimulation parameters over a first-time step.

FIG. 3B shows the utility function (inverted) as a dynamic function of two stimulation parameters over a second time step.

FIG. 3C shows the utility function (inverted) as a dynamic function of two stimulation parameters over a third time step.

DETAILED DESCRIPTION

Figure 1:
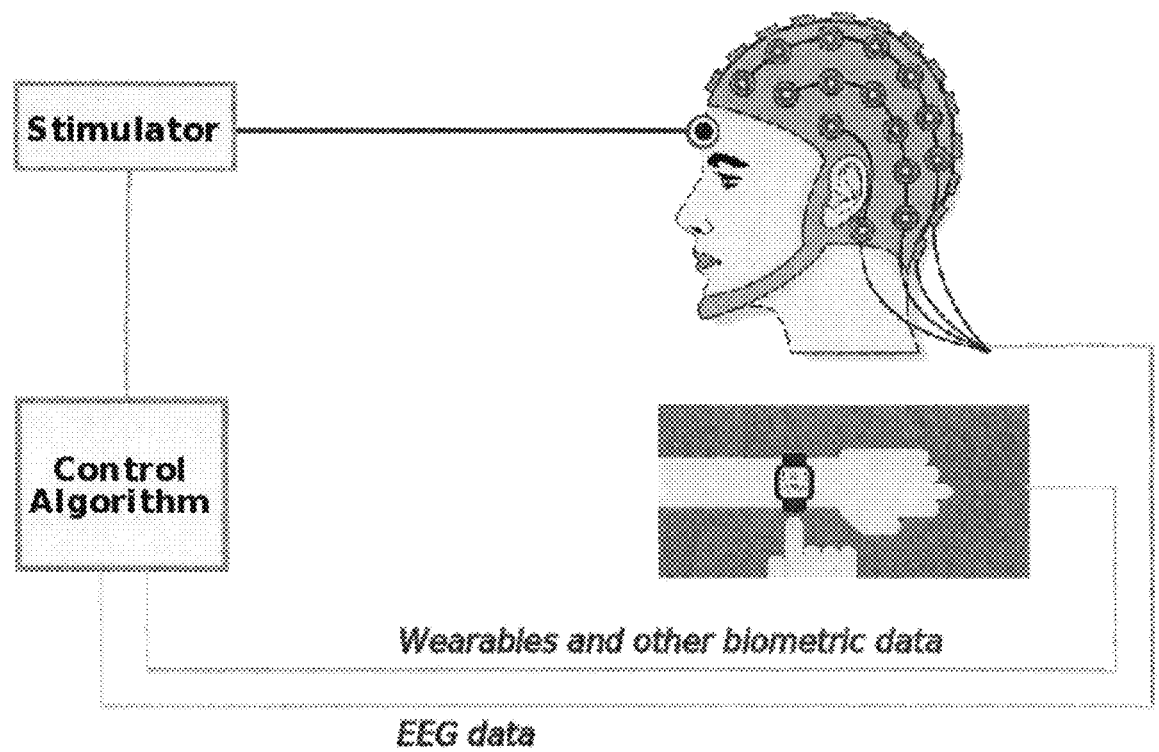
FIG. 1 shows an exemplary brain stimulation system comprising inputs from brain imaging devices (EEG is shown as an example) and from biometrics, the control algorithm, and the stimulation of possibly complex electrode montages or multiple points of stimulation.

Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

FIG. 1 illustrates a first exemplary embodiment of this invention. This closed loop brain stimulation system consists of four primary components. The stimulator, in this case a transcranial electrical stimulation (TES) device directs small currents to a plurality of electrodes on the surface of the scalp. The effect of this stimulation is registered by a brain reading device, in this case illustrated by EEG. The stimulation may also have an effect on biometric data as determined by wearables and the like. The combined set of information, from the brain reading device, and the biometric data, is sent to the control algorithm. This algorithm examines this data, decides how distant it is from a desired state, and adjusts parameters for the next round of stimulation accordingly.

Stimulation of the brain may be carried out by a number of means. Transcranial magnetic stimulation (TMS) creates an electrical field in the brain by means a fast-changing magnetic field. One advantage of TMS is that this relatively large stimulation can directly cause neurons to fire or inhibit the firing of already active neurons; a disadvantage of TMS is that it acts on a relatively large area of the cortex at once, and requires a large electromagnet to do so. A newer technology, transcranial focused ultrasound (FUS) allows a more limited section of the brain to be stimulated, and may prove efficacious in this regard following further experimentation. Deep brain stimulation (DBS) is the most targeted of current stimulation methods, but is this is an invasive technique requiring brain surgery, and is currently only warranted when no other option is available, such as untreatable epilepsy.

In an exemplary embodiment, TES is proposed as the primary means of stimulation. TES consists of small currents, typically <2 mA, applied to the surface of the scalp. One advantage of TES relative to TMS is that the fact that these currents are relatively small means that a portable, non-clinical device, either open or closed loop, can readily be constructed; the latter is described in more detail below. Another advantage of TES relative to TMS is that multiple sites of stimulation can be explored in order to achieve the desired effect; this is described in more detail below, TES comes in two varieties, transcranial direct current stimulation (tDCS), and transcranial alternating current stimulation (tACS). tDCS is primarily used to inhibit or excite a given cortical area, with the prior art indicating that cathodal or negative current stimulation is inhibitory and cathodal or negative current stimulation inhibitory.

tACS is used primarily as a means of entrainment, that is, to tune the relevant cortical area to the native frequency of the stimulation. For example, supposing that one wished to increase the alpha frequency component (8-12 Hz) as revealed by EEG in the frontal as a means of inducing relaxation. One could set the stimulator to 10 Hz, and allow the brain to entrain at this frequency.

Figure 2:
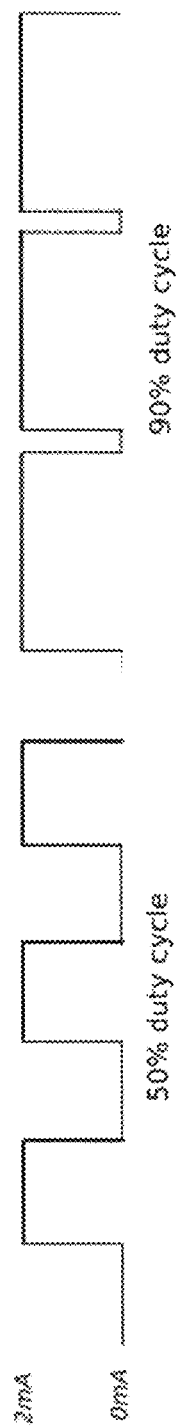
FIG. 2A shows an alternating positive bias square wave current with a 50% duty cycle.
FIG. 2B shows an alternating positive bias square wave current with a 90% cycle.

It is also possible to conceive of a stimulation methodology that smoothly transitions from alternating current to direct current via the relative duration of a square wave within each stimulation cycle. This is illustrated in FIGS. 2A and 2B, showing a 50% duty cycle wave and a 90% duty cycle wave. As one moves towards 100%, the wave moves correspondingly to direct current stimulation. The advantage of the duty cycle methodology is that it provides the control algorithm a continuous means of adjusting between alternating current and direct current via adjustment of the duty cycle parameter; it may be easier to implement the output of the control algorithm as a series of continuous adjustments rather than discrete decisions.

In some embodiments, more than one stimulation modality may be used. Within an open loop methodology, such a combination would be inadvisable, because the interaction between the stimulating methodologies will be unpredictable. However, the closed loop methodology naturally lends itself to this possibility, because continuous monitoring can ensure that the desired effect on the brain is being achieved.

A variety of technologies are available for determining brain state information including function magnetic resonance imaging (fMRI), magnetoencephalography (MES), electroencephalography (EEG), and functional near infrared spectroscopy (fNIRS). Each has advantages and drawbacks. fMRI, which measures the so-called blood-oxygenation-level-dependent (BOLD) response produces a relative activation score per voxel of the brain, and thus is capable of reaching deep i.e. non-cortical structures. However, fMRI is relatively expensive, and has a low time resolution. MES, which measures the aligned magnetic signals among large subsets of neurons, has a better time resolution but requires a very large magnet to pick up the weak magnetic signals of the brain and is both expensive and unwieldy in practice. fNIRS like fMRI measures the BOLD response but with infrared light; this light typically penetrates only a few millimeters of cortical tissue and thus cannot be used to measure sub-cortical response.

EEG is also used to register brain response. EEG works by amplifying the synchronous response of relatively large groups of neurons. The disadvantage of EEG is that is often noisy due to the smearing of the signal by the skull and scalp, and is also subject to artifacts from muscle-generated electrical activity. However, it provides extremely fast time resolution, and in addition produces for each channel a signal that is the sum of alternating waves, the primary frequency components of which are often indicative biomarkers. For example, the magnitude of the delta component (0.5-4 Hz) is indicative of the degree to which the subject has entered non-REM sleep. Furthermore, EEG is a relatively low-cost means of reading brain states, and thus makes it ideal for the proposed portable embodiment of this invention. Furthermore, although only cortical surface signals are present in the EEG signal, quantitative EEG (qEEG) techniques can be used to infer the activity of deeper structures.

It is also possible to combine various brain reading mechanisms to overcome various shortcomings in each. Within the current design, this can be done by expanding the utility function described below to combine the results of measurements over these multiple devices.

One additional issue that arises with closed loop as opposed to open loop methodologies is the need to prevent the stimulation from interfering with imaging methods. For example, TMS generates a large electrical field that will wash out any results from EEG; likewise, the weaker currents from TES also largely obscure this signal. Three methods exist to prevent this from occurring. In the simplest, stimulation and reading alternate such that the time interval between them prevents interference. This achieves the desired effect, but has the disadvantage that the immediate effect of the stimulation, by construction, cannot be assessed—only the effect after the stimulation interval can be assessed. As an alternative, physically orthogonal stimulation and reading methods can be chosen, such that the former does not affect the latter. For example, fNIRS will not be affected directly by either TMS or TES. As an additional alternative, and one also consistent with immediate assessment, the computed effect of the stimulating signal can be subtracted from the read signal to reveal the underlying "true" signal. This method will work well, however, only when this computation is accurate, and effect of the stimulation is not too large relative to the underlying read signal; Miskovic [WO2018067761A1] presents a methodology along these lines.

The control algorithm is the critical element in the closed loop methodology. The purpose of the control algorithm is to adjust the parameters of stimulation to meet a desired goal. In the following discussion, this process is divided into two components: a reference utility function, which the control algorithm is attempting to minimize, and an adjustment method, which determines how the algorithm changes the stimulation parameters in order to achieve this minimization.

The reference utility function can, in turn, be divided into two components. The first component consists of one or more brain biomarkers. The second component includes one or more pieces of biometric data, derived from wearables or otherwise. In general, the reference function will then be a weighted sum of each of these components, or $$U = \Sigma w_i \, \text{abs}(\alpha_i - \alpha_r) + \Sigma w_j \, \text{abs}(\beta_j - \beta_r)$$

where the $\alpha_i$ is the current value of a brain biomarker, $\alpha_r$ is the reference or desired value of that biomarker, $w_i$ is a weighting for that biomarker, $\beta_j$ is the current value of a non-brain based biometric, $\beta_r$ is the reference or desired value of that biometric, and $w_j$ is the weighting of that biometric in the utility function.

Thus, U will achieve an absolute minimum if and only if all of the $\alpha i$ equal the $\alpha r$ and when the $\beta j$ equal the $\beta r$, that is, when all of the biomarkers and biometrics are in the desired state. Note that in most cases, this will not be possible, and the goal is to simply minimize U, not make it vanish. Note also that the $\alpha$ and $\beta$'s may be operating at different time scales; for example, a brain-based biomarker may reveal the immediate brain state, while a biometric such as relative physical activity may be over minutes or longer.

The $\alpha$'s in the utility function are considered first. A brain biomarker in general is defined as a measurable state of the brain. It may be a local state, that is, a measure of activity or dynamics within an area of the brain with distinct anatomy or neurophysiology. For example, it could be the activity in the right dorsolateral prefrontal cortex (rDLPC), or activity in the visual area V1 of the visual cortex, or dominant frequency in right parietal cortex. It may also be a measure of relative values between two areas, for example, asymmetry between activity in left and right prefrontal cortex. It may also be a measure of functional interactivity between two or more areas of the brain, representing not merely the correlation between these areas, but the inferred degree of causal interactivity, and the direction of this causality. Finally, it may refer to a global state of the brain; for example, one can speak of the relative metabolism of the brain in the non-REM sleep state relative to the awake state, or the overall functional connectivity differences between these states.

Biomarkers are of interest because they may be related to desired or undesired psychological states. For example, low activity in the left prefrontal cortex relative to right has been found to be correlated with MDD. In contrast, suppression of activity over the entire left frontal hemisphere has been found to correlate with bursts of creative thought. Of crucial interest is the distinction between biomarkers that are merely correlated with a cognitive or affective state and those that have causal efficacy with respect to this state. If the former, then influencing the biomarker will by construction have no influence on the associated mental states. In many cases, however, the causal connection does exist, as revealed by experiments that perturb the biomarker, and later assess the resultant mental state. For these reasons, in some embodiments, the degree of causal influence of the biomarker on the mental state is assessed in advance of the stimulation procedure.

Differing neuroimaging methods reveal different biomarkers. In addition to these "raw" statistics, a number of inferred statistics may also be generated. In the simplest case, the relevant biomarker is not apparent in the time domain but rather in the frequency domain. Fourier-transformed EEG signals for example are commonly used to assess drowsiness, degree of concentration, and synchrony between neural modules.

Other more complex derived statistics are also possible. For example, functional connectivity between brain regions has been found to be indicative of a number of abnormal mental states. Functional connectivity is not a direct characteristic of a neuroimaging modality, but may be calculated by derived from the data by observing the degree to which a neural module has causal influence over another module.

In some cases, the biomarker may not always be obvious from the data at hand, nor can it be motivated by theoretical underpinnings. However, in some embodiments, a discrimination function acting as an effective biomarker may be produced by the following procedure. Let us assume that the aim is optimize a task, for which performance is recorded. This performance statistic may be either a simple Boolean indicating success or failure, or it may be a continuous measure indicating degree of success.

The collection of brain states as revealed by the appropriate imaging method associated with each such statistic will then comprise of a set of examples that constitute the input to a machine-learning algorithm. The purpose of this algorithm is to predict the performance statistic from the brain state with as high degree of accuracy as possible. A number of algorithms in the prior art may be considered such as neural networks, decision trees, or the family of deep learning algorithms.

The end-product of such a procedure is a model that acts as an effective producer of a biomarker, regardless of whether that model is easily interpreted or not. That is, for each brain state as revealed by the imaging modality, it will generate a numerical evaluation indicating the degree to which the desired brain state is achieved. This evaluation can then be used as the critical element that the control algorithm is attempting to optimize.

Biometrics, the β's in the utility function described above, like brain biomarkers, come in two forms, raw or unadulterated fields and calculated fields. The former includes measures such as heart rate, respiration rate, galvanic skin response (GSR), and blood sugar levels. The latter include constructed fields such as sleep quality, degree of activity, balance, and possibly more advanced measures based on camera-provided data such as degree of engagement with other people. Constructed fields that measure short and long-term states are especially important in assessing the effect of any form of stimulation on affective disorders such as depression, and can provide important clues as to whether the treatment regime is working appropriately.

The control algorithm computes the utility function U and attempts to adjust the parameters of stimulation to reduce this quantity. Stimulation parameters are modality dependent. In the primary embodiment of this invention using TES as the stimulation method, these include, per stimulation electrode, the placement of the electrode, the length of the stimulation period, the frequency of the stimulation, the magnitude of stimulation, the size of the duty cycle, and whether the stimulation is cathodal or anodic in the case of non-alternating current TES.

It is also possible to have complex montages of stimulation, that is, over more than one electrode. Critical to the proper operation of this complex multiple input multiple output (MIMO) system is a control algorithm that guides the stimulation parameters over the electrodes such the quasi-minimum of the utility function is reached without undue difficulty.

Figure 5:
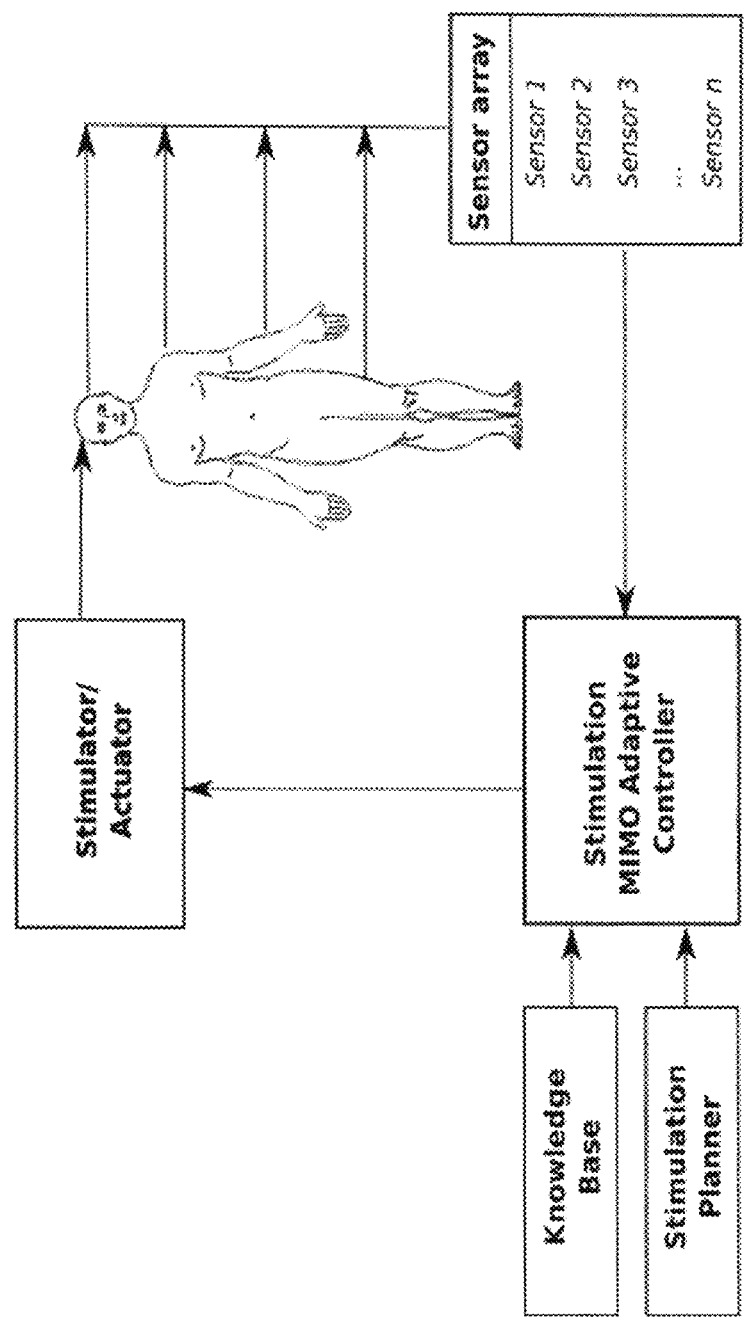
FIG. 5 shows the general architecture for a multiple (Multi Input, Multi Output MIMO)-adaptive control loop mechanism.

FIG. 5 shows the general architecture for a multiple (Multi Input, Mufti Output MIMO)-adaptive control loop mechanism that enables tuning of the models on the basis of newly acquired, as well as archived knowledge bases. Each link actually represents vectorial quantities, for example the links from the sensors array module to the computer, indicates a large variety of potential signals, both analog and digital. The entire computational part of the system is implemented on a processor, which will be carried on the body of the user. Such processor will have local memory, power, communication channels, and downloading program updates capabilities. Each of the components of this architecture is now described.

Stimulation planner. The stimulation planner is designed on the basis of clinical expertise and realizes the knowledge relevant for a specific clinical or well-being application. This knowledge includes biomarkers specific to a given pathology, for example, left-right frontal activation asymmetry in the case of depression, or the putative elevated theta to beta ratio in the case of ADHD. These quantities may be determined by a clinical expert and become available as target values for the control loop. If and when new knowledge gets acquired, such quantities may be updated for improved execution for the entire system. This module generates the desired values for all features extracted from the biomarkers on the basis of clinical knowledge base for the targeted clinical application.

Stimulation multi input multi output (MIMO) adaptive controller. This module implements the entire control system which accepts the desired values from the planner, the sensory values from the sensors array, communicates with the knowledge base and computes the stimulation patterns which is sent to the stimulator/actuator. See detailed description in FIG. 6 and below.

Sensors array. The sensor array will be placed on the patient's body and within his/hers immediate environment and surrounding e.g., (cameras in the room, etc.). This module contains an array of both neural monitoring sensors as well as behavioral and physiological sensors together with their data normalization, data acquisition and data conversion components.

Knowledge base. The knowledge base may be onboard or accessible in databases via internet access. The knowledge base module contains both local archives of accumulated patient-specific data as well as online access to databases archives, and additional knowledge base information sources to be used in online performance of the entire system. The communication is bi-directional, both for downloading updated knowledge, as well as for sending back newly acquired information and features to update the knowledge base.

Stimulator/Actuator. The stimulator actuator may include various modalities such as magnetic, electrical (both DC and AC), ultrasonic, heat, sound, music, video, rhythmic, as well as other potential stimulation mechanism to one's homeostasis. This module implements the amplification, signal conditioning and actual generation of the energy required to stimulate the brain via the array of electrodes or other actuators that are mounted on the person's body/skull. Various configurations of such stimulators will be required depending on whether it is an outpatient, clinical, hospital or in-home or leisure activity.

Figure 6:
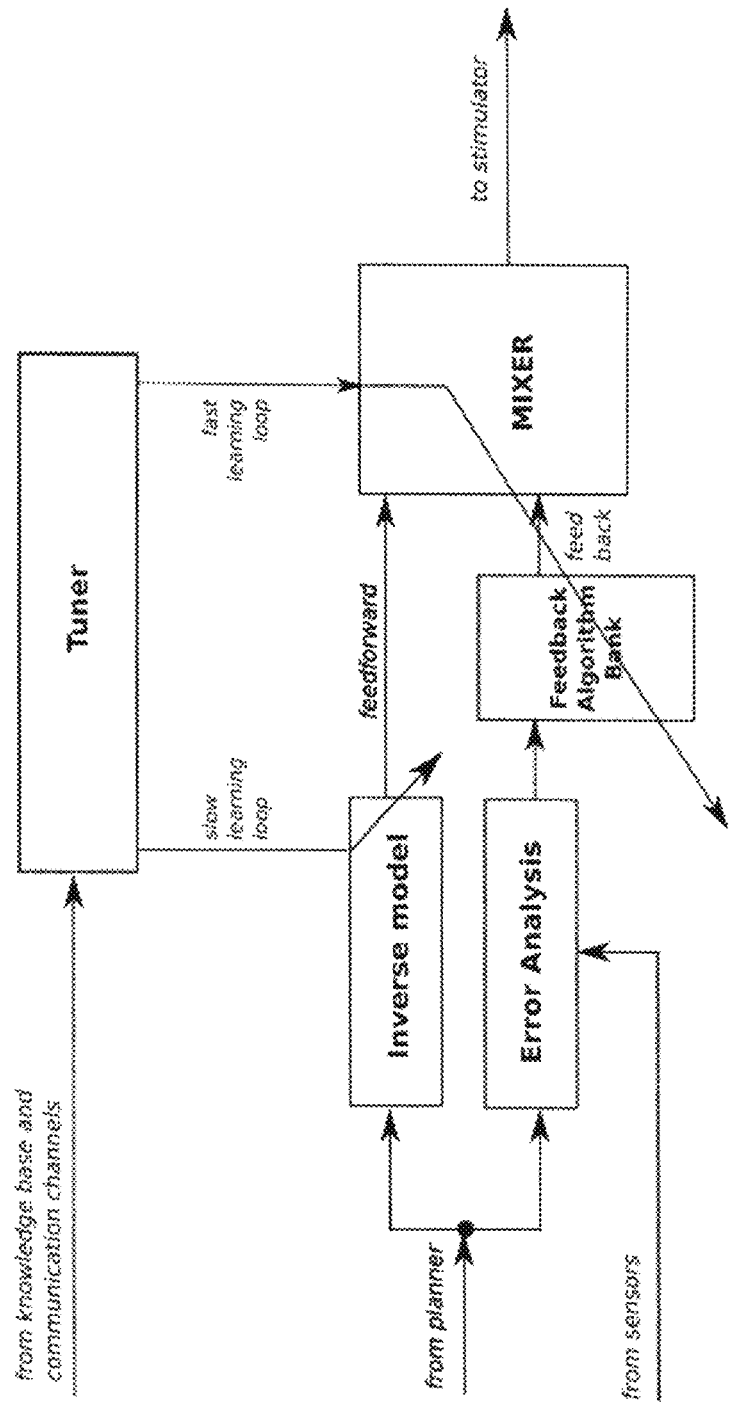
FIG. 6 details the inner signals and information flow.

FIG. 6 details the inner signals and information flow. This control system accepts sensory value from the sensor array unit, desired biomarker and feature values from the stimulation planner unit, knowledge from the knowledge base via the communication channel (as needed), computes the desired stimulation pattern that include sites, frequencies, desired power, specific electrode configuration, and in general determines the specific stimulation wave forms patterns as both special and temporal vectors. We describe below the function of each of the specific modules contained in this multi-input multi-output adaptive controller. Each such module relies on advanced control technologies in the prior art including: adaptive control, system identification online, feed-forward control, feedback control, optimal control, machine learning deep learning, and the integration thereof. We claim that the combination of such technologies is, however, new and unique.

Tuner. This module receives data from the knowledge base as well as onboard memory access. It manages two learning/tuning loops. The slow-learning loop adjusts an onboard inverse model, which is needed for computing the feed-forward component of the stimulation control. The fast learning loop is managed in order to update online the proper mixing of the feed-forward and the feedback signal, as well as for adjusting the feedback specific algorithm, its parameters, and the selection of whatever gain scheduling or specific feedback mechanism. The time constants for the fast-learning loop are in the order of the therapeutic or well-being session (seconds or minutes, at most hours) while the time constants for the slow-learning loop is the adjustment of cumulative expertise over the entire lifetime of the product and the experience of thousands of patients/users. The technology implemented in the tuner relies on the mature system identification theory from dynamic control systems.

Inverse model. This module receives the desired features from the planner and updated parameters from the tuner (online) and computes the feed-forward signal to be sent to the control mixers unit. The technology implemented in this module relies on the mature control system technology (see for example the description of the general sequence of operations in closed loop system discussed above). See also the use of internal model control (IMC) for realizing this module.

Error analyzer. This module is responsible for receiving the data from the sensors, extracting relevant features, comparing these features to the desired values received from the planner module A, and determining the intensity of the desired feedback gains. For example, when the deviation between actual and desired features is large and volatile, strong gains are required as well as potentially involvement of integral and derivative and higher-order dynamic compensation (PID) while when the errors are small, the feedback gains may be reduced, the derivatives eliminated, and stronger reliance from the feed-forward signals from module B2 may be assumed. The technology implemented in this module relies on mature control system technology.

Feedback algorithm bank. This local database contains a repertoire of feedback strategies such as P, PD, PI, PID, optimal control, LQG, LQR, IMC, neuro-control, predictive-control, adaptive-control, etc. from which the proper and specific feedback control algorithm will be retrieved for that specific configuration as identified by the error analyzer module. Once a specific algorithm is selected, the error from this module gets processed and sent as the desired feedback compensation signal to the mixer module. This module gets monitored by the tuner and obtains frequent updates based on the cumulative experience of the specific patient/user and the population database. The technology implemented in this module relies on the mature control system technology.

Mixer. This module receives the proposed feedforward compensation from B2 and the proposed feedback compensation from the feedback algorithm bank and on the basis of the tuning signal from the tuner, determines the actual current-specific spatial and temporal stimulation pattern vector, which gets sent to stimulator/actuator. The strategy for the proper level of mixing between the feedforward and the feedback depends on the level of accuracy of tracking of the desired biomarker feature values. For example, when tracking is poor and the actual features obtained from the sensors are far from their desired values, the mixer emphasizes the feedback signal and de-emphasizes the feedforward. In contrast, when tracking is accurate and the patient/user generates biomarkers that are consistent with the desired therapy/wellness session parameters, the feedback is diminished while the feedforward is emphasized to maintain such acceptable regime. This technology relies on several decades of experience in designing and using online adaptive controllers for non-linear dynamic systems. The technology implemented in this module relies on the mature control system technology.

The closed loop stimulation paradigm, comprising a plurality of brain-based biomarkers, a plurality of biometrics, a stimulation method, a brain reading method, and a control algorithm that adjusts a plurality of stimulation parameters to reduce the distance between the current state of the brain and the current state of the biometric measures and the desired state of such produces a number of advantages over the corresponding open loop system. These include the ability to adjust to differences in individual neuroanatomy and neurophysiology, the ability to dynamically alter the stimulation as the brain adjusts to the stimulation, the ability to combine various strands of input, brain and body-based into a single formula for optimization, and the ability to work with complex montages of stimulation; each is now considered in turn.

An open loop stimulation system works by computing a fixed initial stimulation regime that is, by definition, not amenable to feedback. This regime can and often does include individual differences; for example, differences in the location of the premotor cortex determine the desired stimulation location for TMS. However, when such information is lacking, or is difficult to compute, as is most often the case with differences in brain physiology and dynamics, then the initial stimulation regime is incapable of adjusting to this circumstance. In contrast, a closed-loop system will intrinsically take into differences in anatomy, physiology by virtue of altering the stimulation parameters according to what works in the given circumstances for the current patient. In principle, the path from the current state to the desired state may and often will differ radically depending upon these differences; thus, the stimulation regime is not fixed, but is tailored to the idiosyncrasies of each individual patient.

In an open loop system, once a stimulation regime has been pre-computed, whether it takes into account individual differences or not, it cannot be altered because there is no available information upon which to make this alteration. Yet the brain itself is a complex dynamic system, and will respond in differing and often unpredictable ways to a stimulation regime. Thus, the task of achieving a desired brain biomarker is not merely a matter of attempting to bridge the gap between the initial state and the desired state by a set of "personalized" stimulation parameters, but one that also continuously adjusts these parameters as the dynamics of the brain is altered. To take a simple example, habituation to all forms of stimuli is a universal characteristic of brain response, but one that varies in intensity from person to person and stimulus to stimulus. Brain stimulation must therefore adjust for this habituation, and moreover in a manner that takes into account not only individual differences in tonic habituation levels, but differences in responses as the stimulation regime proceeds.

The process of pre-computing a desirable stimulation regime without feedback from the environment is compounded when that environment includes multiple sources of input, not merely a single-brain based signal or constructed feature thereof (the $\alpha$'s and the $\beta$'s in the utility function above, respectively). Consider that for each type of biomarker or biometric potentially affected there will be an error, and in general a set of parameters that minimizes one such error will not do so for another error. Therefore, the set of parameters that achieve a minimum of the utility function is likely to be narrower, and less likely to be able to estimable from the outset. This reduction in the margin of error further motivates the need for a control system that is able to hone in on the relatively narrow set quasi-optimal stimulation parameters.

The process of pre-computing a desirable stimulation regime without feedback from the environment is made that much more complex when there are multiple stimulation parameters within a given stimulation point or multiple points of stimulation each with its own set of parameters. FIGS. 3-3C illustrate the distinction between tuning a single parameter to optimize the utility function in a static situation (FIG. 3), and optimizing 2 parameters in a dynamic environment which changes over time (FIGS. 3A-3C); for the purposes of these figures the utility function U is inverted, i.e., the goal is to maximize this function. Even with a static situation, that is, one contour graph on the bottom of the figure, finding the right combination of parameters is made more difficult in the multidimensional case, as the search space is larger, and in addition there are more local or pseudo-minima (in this case 3). In general, the utility landscape as a function of the simulation parameters will be highly fluid, and there will be many more than the 2 parameters shown in this simplified diagram, especially when complex stimulation montages are considered, making it that much less likely that a pre-computed stimulation regime will achieve a desirable outcome, and necessitating a closed loop driven search for such.

As one instance of the control embodiment, consider the special case in which a single stimulation parameter (for example, stimulation frequency) is adjusted in an attempt to improve the desired outcome as represented in the utility function. This may be achieved in the absence of a priori knowledge of the causal determinants of the utility function as follows. Choose a value v for this parameter and two additional values v+Δ and v−Δ for the initial stimulation block. Then among these 3 stimulation regimes, choose the one that produces the best utility score. This becomes the next center of stimulation, with the Δ's now added and subtracted to this value. In addition, at each block of 3 stimulation values, reduce Δ by a factor $\alpha<1.0$, to allow the system to approach a local optima of the utility function.

If neural dynamics are relatively stationary, then the system will "home in" on the best response in a relatively short period of time with a relatively small value of α; when the brain is changing state relatively rapidly, as will often be the case, it may be desirable to use a larger value of α so that the system can adjust more readily to these changing dynamics.

In another embodiment of this control algorithm, if the system happens upon a particularly good value of the utility function, as judged in comparison to past values of this function, then a may be lowered by a constant factor so as to hold the system steady in this desirable state. As before, the degree to which this lowering is instituted depends on the stationarity of the underlying neural dynamics.

In the following, we consider the application of various embodiments of the closed loop paradigm to the treatment of brain-based pathologies, as well as enhancement of non-pathological brain-based conditions, although this list should be seen as exemplary, rather than exhaustive. This invention in principle can be applied to a wide range of pathologies and enhancements beyond the embodiments discussed, with the appropriate changes in stimulation and brain-based and other inputs, but without fundamentally altering the operation of the control algorithm.

For the treatment for major depressive disorder with TES and EEG, the key brain-based biomarker is the ratio of left to right dorsolateral pre-frontal activity, which has been found to be reliable indicator of this condition, and is the basis of the current FDA-approved TMS treatment for depression. Relative activity between left and right cortices is assessed indirectly via the presence of alpha, which in turn is inversely correlated with neural activation. Thus, the goal is to boost alpha in the right cortex (thereby inhibiting activation), and decrease alpha in the left.

In one embodiment, this is done simply by applying anodic (i.e., positive) stimulation to the left prefrontal cortex; the control algorithm in this case adjusts the electrode montage delivering the stimulation as well as other real time parameters stimulation intensity. In another embodiment, frequency entrainment is used to increase alpha in the right front cortex, that is, the effect by which the brain will come to produce the same frequency at which it is stimulated. This has been shown to have maximal effect when the brain is stimulated at the so-called individual alpha frequency (IAF), that is, the natural alpha frequency in the 8-12 Hz band which dominates for a patient. In this case, the goal of the control algorithm is to initially assess this frequency, and then deliver stimulation at the same frequency. The control algorithm may then adjust the frequency and/or the other parameters with a view of keeping the symmetry between alpha (and therefore activation) as high as possible. In yet another embodiment, both left and right clusters of electrodes stimulate at once in order to achieve the same effect. The complexity of this montage normally prevents it from being efficacious in the open loop scenario; however, with closed loop monitoring it has the potential to be more powerful than stimulating on either side of the cortex alone.

Boyden [US2008/0319505] discusses entrainment and related effects but does not discuss a general utility function nor a general control algorithm to maximize this function. Without these elements of the invention, the scope of application is considerably narrowed. In many cases, because of the complex dynamic interaction over the approx. 100 billion neurons in the human brain, the relation between input stimulation parameters and brain output will itself be complex, and the one will not necessarily mirror the other. Katz [2002/06488617] allows for this more general situation, i.e., where the inputs stimulation and output response have no obvious relation, but only in the context of transcranial magnetic stimulation (TMS), and does not treat the notion of additional sensors that may be folded into the utility function.

In another embodiment for pathological brain function, attention-deficit hyperactivity disorder (ADHD) is the target condition. ADHD is characterized by excessive activity, but with the inability to focus this activity on a cognitive task. There is some evidence that an elevated ratio of cortical theta EEG waves (4-7 Hz) to cortical beta waves (12-30 Hz) is a reliable biomarker for this condition, although this may be complicated by alpha (8-12 Hz) activity. Thus, better results may be obtained by first producing a model-based biomarker in accordance with the procedure described above.

Regardless of the precise biomarker, a closed loop system that entrains at the desired frequencies, and leverages the control algorithm to hold these frequencies as steady as possible is a viable candidate for therapy. As before, individual differences as well as changes in brain dynamics as treatment ensues makes it unlikely that an open loop system that did not differentiate between patients and could not change over time would be as efficacious as the proposed closed loop method.

In another embodiment for enhanced brain function rather than pathology correction, a closed loop brain stimulation system may be used to enhance cognitive activity on a particular task. Current methodology for achieving this, whether it be for purely perceptual tasks, or for more complex cognitive tasks, is a two-step process. First, the activity focal points in the brain over a population of subjects on the task is determined by averaging over the EEG or other data over a number of subjects. The identified areas are then subjected to excitatory stimulation with tDCS, on the theory that Hebbian associative learning is proportional to the degree of activity of pre and post-synaptic firing rates. In effect, tDCS is lowering the threshold for one or both of these, increasing firing, and therefore increasing learning rates.

A closed loop system can improve on this process in the following way. Rather than determining a mean activation locus or loci over a number of subjects in a pre-processing step, which by construction washes out individual differences, the precise locales of activity "hot-spots" can be identified for each subject. These loci can then be stimulated in a way that accommodates the differences in processing of the task for each subject. In addition, these loci may change during the course of the task, and in a way that also differs from subject to subject. If this change is also measured by EEG or the appropriate imaging modality, the stimulation locations can be dynamically altered during the task to achieve maximal effect.

In another enhancement modality, TES combined with EEG can be used to enhance creative endeavors. These may include directly artistic endeavors such as paining and music composition, but also activities with a partial cognitive component such as difficult problem solving or complex associative tasks. Research indicates that the suppression of the left cortical hemisphere, in part or as a whole, and the enhancement of activity in right hemisphere can enhance tasks of this nature.

Accordingly, the goal of a closed loop system is similar to that of the case of MDD, except that the hemispheres are switched. Thus, a similar, closed loop strategy applies here, with similar justification. Individual differences will change the parameters of stimulation to achieve maximal effect, and differing dynamics will also lead to differences in stimulation over time. In addition, closed loop stimulation motivates the possibility of simultaneous left hemisphere suppression and right hemisphere elevation, mirroring the possibility of this dual strategy for depression.

In another enhancement modality, closed loop stimulation can be used to enhance motor skills. Such skills present an interesting problem because there is great variability in performance not merely between people, but within a given skill for a given person from attempt to attempt. Free throws in basketball and tennis serves are two such examples, although more dynamic motor actions could also be considered. One closed loop method for approaching this problem is as follows. Observe with EEG or another imaging modality a number of positive (that is successful) and negative (that is, unsuccessful) attempts at the given task. From this, derive a biomarker that maximally distinguishes between these cases; in the most complex case this biomarker may be an inductive model built from these positive and negative examples as previously described. This biomarker becomes the desired state, and the goal of the closed-loop system then is to reduce the distance between the current state and this desired state. Additional feedback to the control algorithm may also be provided by the new success rate after the stimulation regime and may help further refine the stimulation regime.

Figure 4:
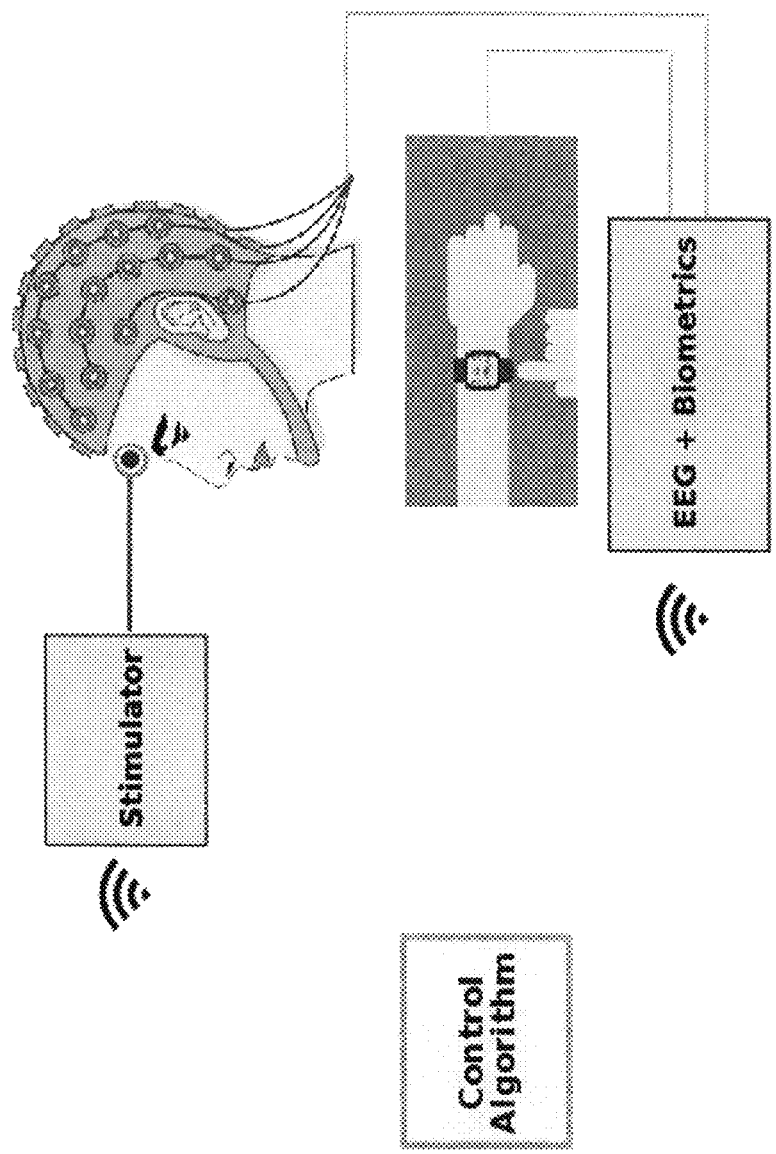
FIG. 4 shows a portable embodiment of this invention wherein the control algorithm receives EEG/imaging and biometric data wirelessly, and directs the stimulator to adjust the stimulation parameters by wireless means.

In some embodiments, the apparatus in FIG. 1, and by extension, the various embodiments previously proposed, can be converted into a portable device for home use, or for more dynamic activities like sports or other motor tasks. Apart from ergonomic concerns, the key step in this process is shown in FIG. 4. Here, the connections from the incoming data, EEG and biometric to the control algorithm have been replaced by a wireless transmission system. Likewise, the connections from the control algorithm to the stimulation device can also be made wireless. This will "untether" the subject from the control apparatus, allowing more freedom of movement, and a generally more portable experience. In some embodiments, the control algorithm itself can be embedded in a chip in either the stimulator or the brain imaging or wearables, further reducing the size and complexity of the system.

In yet another embodiment, the frequency profile of the brain as revealed by EEG is manipulated by the closed-loop system. The relative power of various frequency bands (as revealed by Fourier transforms and other mathematical methods) is a fundamental aspect of the EEG signal, and revelatory of many associated psychological states. For example, relatively high levels of alpha (the 8-12 Hz band) are often associated with the desired meditative state, and therefore it is the goal many neurofeedback devices to enhance activity in this band. Likewise, activity below 4 Hz (the delta band) is associated with non-REM deep sleep. The utility function in these cases is simply proportional to the amount of power in a given band relative to the total power across the spectrum, in the Fourier transformed space over a given time period.

The division of the power spectrum into distinct frequency bands is somewhat arbitrary and therefore in some embodiments a measure with less presuppositional basis may be preferred. One such measure is the center of gravity of the power spectrum, computed by the weighted sum $$P=\Sigma w_i f_i,$$

where the $w_i$ represent the relative power of each frequency $f_i$ in the spectrum. In practice, the measure is normalized by having the $f_i$ be narrow but discrete frequency bands, and by having the $w_i$ sum to 1.0. The utility function can then be designed to lower or to raise this measure, with the control algorithm adjusted accordingly.

The adjustment of the mean frequency response and/or the enhancement of a particular band of frequencies historically was the domain of neurofeedback techniques. These typically provide the subject with visual or other feedback of the power spectrum or subset thereof in order to allow to give the subject more direct access to the dynamics of their brain processes so that they may adjust them accordingly. For example, Ayers [US1989/04919143A] gives both auditory and visual feedback of the degree of alpha and other band powers to the subject. However, there is no guarantee providing a window into one's own brain's response will allow one to fundamentally change its behavior. The current paradigm, closed-loop brain stimulation, may therefore be construed as an embodiment in which active external stimulation partially forces the brain into a given response.

As an example of such a process, consider the results provided by the simplified general algorithm described above as applied to minimization and maximization of the power spectrum center of gravity as given by the measure of the equation above with an initial stimulation frequency of 8 Hz, an initial $\Delta$ of 2 Hz, and a reduction factor $\alpha$ of 0.5. That is, the left frontal cortex of the brain for this subject was initially stimulated at 6, 8, and 10 Hz, and then the frequency that produced the best mean response amongst the neighboring reading electrodes (lowest center of gravity for minimization, and highest for maximization) was chosen as the next starting point. The frequencies around this new frequency were then stimulated, with these surrounding frequencies now 2 Hz×0.5=1 Hz away from this central frequency, etc.

Figures 7A, 7B:
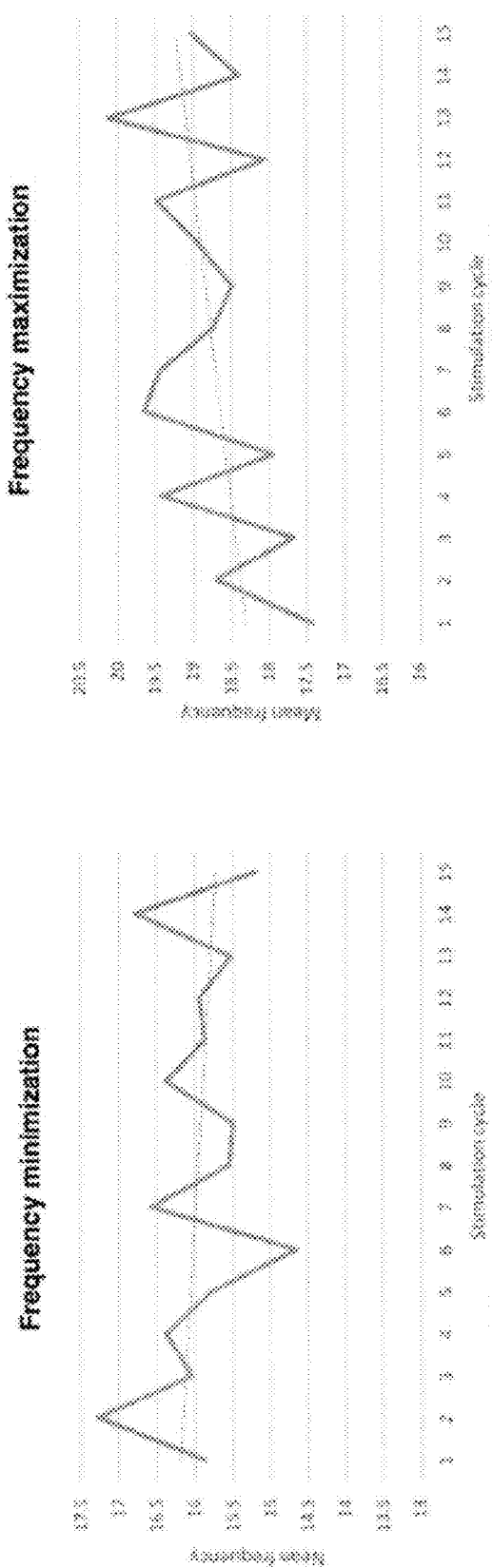
FIG. 7A shows the result of a stimulation experiment that attempts to minimize the mean EEG frequency response of the brain via closed loop tACS stimulation.
FIG. 7B shows the result of a stimulation experiment that attempts to maximize the mean EEG frequency response of the brain via closed loop tACS stimulation.
Figure 8:
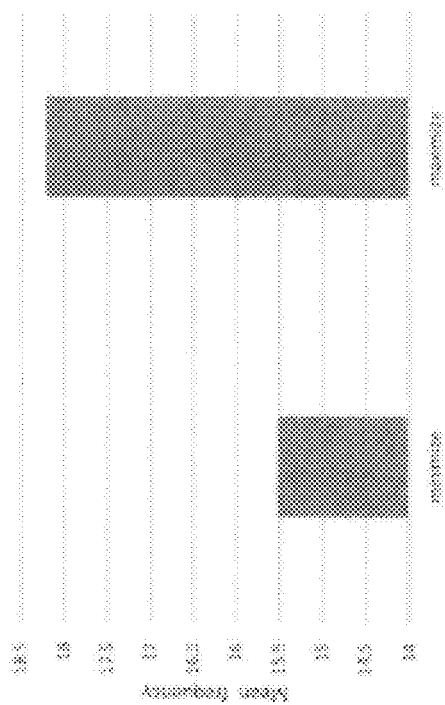
FIG. 8 summarizes these results and shows the mean difference in response between the minimization and maximization trials.

The graph of FIG. 7A shows the average of three trials on a single subject as in all the data reported here, shows the result of minimization after 5 blocks of 3 stimulation frequencies following this algorithm. Note that trend line (dotted) does indeed show that the mean frequency of the spectrum reduces over time. Likewise, when the goal is frequency maximization, there is a steady increase in the mean frequency response of the brain as revealed by EEG, as shown on the graph of FIG. 7B. FIG. 8 summarizes these results by showing the average mean frequency over all 15 stimulation periods for both minimization and maximization. The overall maximization response is approximately 20% higher than the minimization response, demonstrating the efficacy of the closed-loop approach with respect to frequency adjustment.

Figure 9:
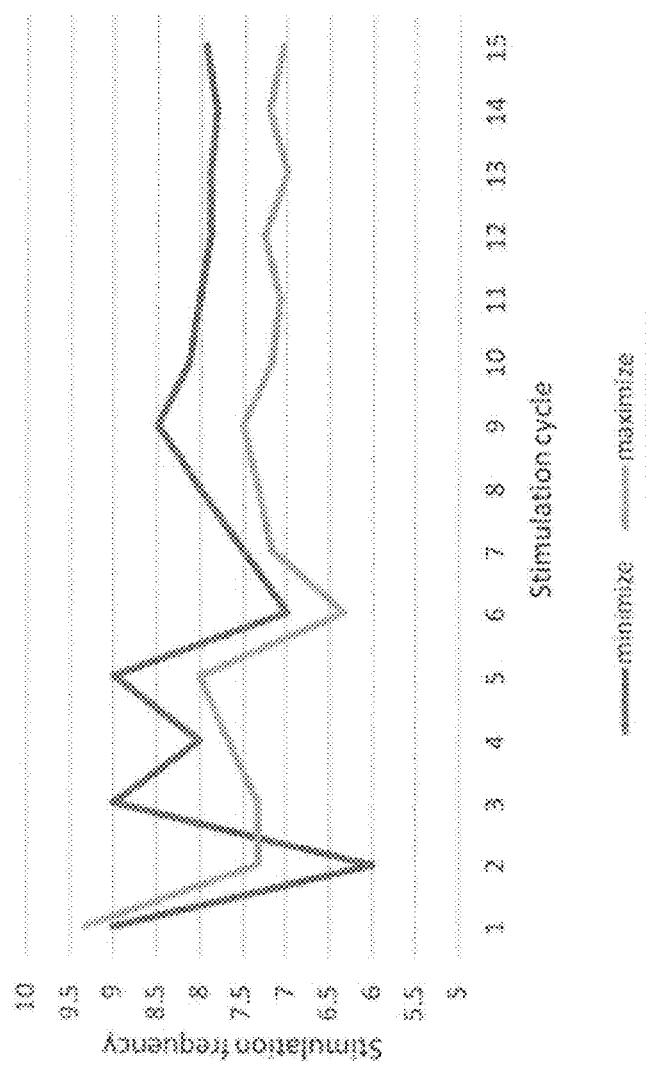
FIG. 9 illustrates the path of stimulation frequencies taken for both minimization and maximization; the latter is lower than the former.

Furthermore, the importance of a general control algorithm as opposed to an a priori notion of how to adjust stimulation to achieve a certain goal is well-illustrated by this example. FIG. 9 shows the stimulation frequency path chosen by the algorithm for both minimization and maximization. Note that the frequency of stimulation for maximization end up being lower than that for minimization. This is the opposite of the effect that one would expect if entrainment were the driving force in determining brain frequency, and partially validates a closed-loop approach that works with weak or absent a priori assumptions regarding the interaction between brain stimulation and neural dynamics.

Figures 10A, 10B:
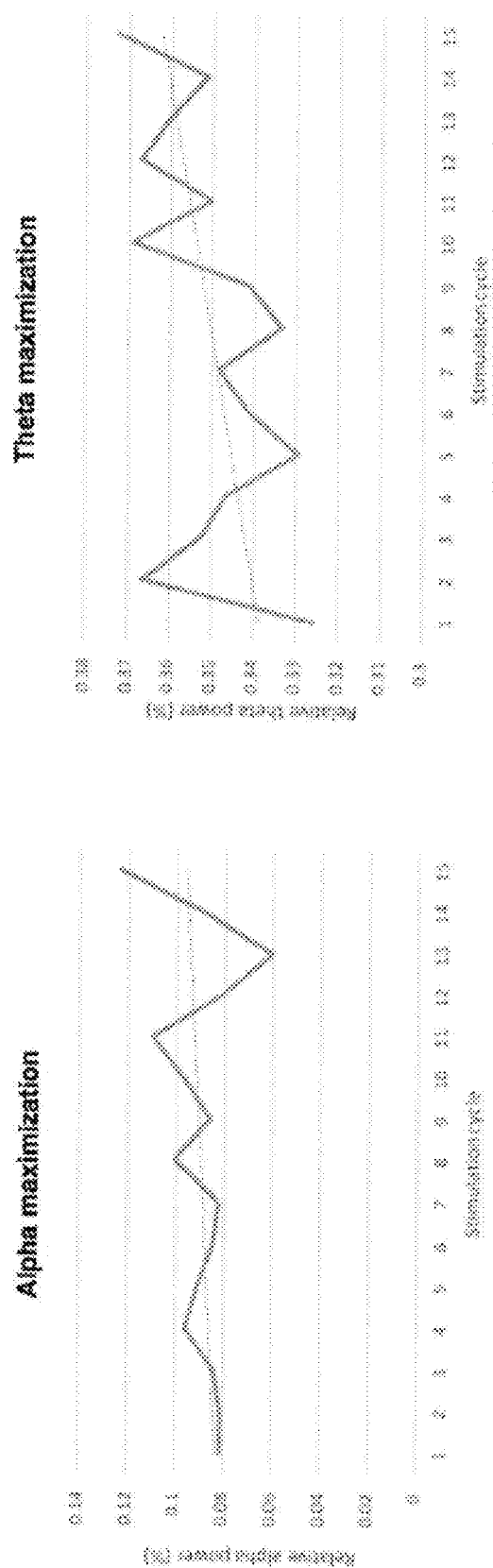
FIG. 10A shows the results of a closed loop stimulation experiment in which the goal is maximize relative power in the alpha band.
FIG. 10B shows the results of a closed loop stimulation experiment in which the goal is maximize relative power in the theta band.

FIGS. 10A and 10B show the apparatus with the simplified algorithm affords a similar response when the goal is to enhance a particular frequency band. Here, the goals are alpha (8-12 Hz for current purposes) maximization, shown in FIG. 10A, or theta (4-8 Hz for current purposes) maximization, shown in FIG. 10B. In both cases, there is a steady albeit non-monotonic rise in the relative power in each of these bands as the trial proceeds. These results encourage the notion that cranial electrical stimulation with the appropriate control algorithm can either augment or supersede the method of merely presenting the current brain state to the user in visual or other form as done in conventional neurofeedback paradigms.

It will be further understood that various changes in the details, materials, and arrangements of the parts which have been described and illustrated in order to explain the nature of this invention may be made by those skilled in the art without departing from the scope of the invention as expressed in the following claims.

We claim:

1. A closed loop brain stimulation system, comprising:
   means for reading electrophysiological signals from the brain;
   means for reading other biometric signals;
   means for stimulating the brain;
   means for mixing a feed-forward signal and a feedback signal for generating a signal for transmission to the means for stimulating the brain;
   an inverse model module configured to receive desired features and compute the feed-forward signal; and
   a control algorithm that dynamically adjusts a mixing process affecting brain stimulation to minimize a reference utility function, including a cumulative measure of the difference between the current and desired brain states, and current and desired biometric states.

2. The system according to claim 1, wherein the algorithm is adapted to assess, via internal model, the effect of perturbing the multiple stimulation parameters, singly, or in groups, and adjust the parameters to maximally influence a given biomarker in a desired direction.

3. The system according to claim 1, wherein, when the brain is stimulated by the means for stimulating the brain at an individual's dominant frequency in the 8-12 Hz band, the control algorithm assesses that dominant frequency, and then transmits a signal to the means for stimulating the brain at that same frequency.

4. The system according to claim 3, wherein the control algorithm adjusts the frequency.

5. The system according to claim 1, wherein the algorithm is adapted to examine data from the signals, determines brain state, and adjusts parameters for a subsequent round of stimulation in order to modulate the brain from the determined state to the desired state.

6. The system according to claim 1, wherein the system accounts for individual differences in neuroanatomy and neurophysiology.

7. The system according to claim 1, wherein the system dynamically adjusts over time within an individual profile.

8. The system according to claim 1, wherein the system reads from multiple sources of inputs, including multiple brain-based biomarkers and multiple biometric signals.

9. The system according to claim 1, wherein the system optimizes with respect to multiple stimulation parameters and complex montages of stimulation.

10. The system according to claim 1, wherein the system is adapted to treat major depressive disorder with TES and EEG as the respective stimulation and reading methods, and with the incorporation of other biometric signals indicative of the depressed state.

11. The system according to claim 1, wherein the system is adapted to treat ADHD with TES and EEG as the respective stimulation and reading methods, and with the incorporation of other biometric signals indicative of the hyperactive state.

12. The system according to claim 1, wherein the system is adapted to enhance cognitive and/or perceptual skills, by first identifying the activated areas of the cortex during these processes, in an individualized fashion, and then stimulating them in order to accelerate associative learning within the task.

13. The system according to claim 1, wherein the system is adapted to enhance the suppression of the left hemisphere and/or the enhancement of the right hemisphere by various monitored means in order enhance creativity in open ended task such as drawing and more closed tasks such as difficult problem solving.

14. The system according to claim 1, wherein the system is adapted to enhance motor skills by first constructing an individualized biomarker model distinguishing between brain states that lead to successful motor events and those that don't, and then applying the closed loop system to achieve these successful states.

15. The system according to claim 1, wherein the system is portable.

16. The system according to claim 1, wherein the system adjusts stimulation frequency to effect a minimization or maximization of mean frequency response, or to enhance the relative power of a particular band of frequencies.

17. A closed loop brain stimulation system, comprising:
   means for reading electrophysiological signal from the brain;
   means for reading other biometric signals;
   means for stimulating the brain; and
   a control algorithm that dynamically adjusts a mixing process affecting brain stimulation to minimize a reference utility function, including a cumulative measure of the difference between the current and desired brain states, and current and desired biometric states, wherein the algorithm effects a continuous adjustment between alternating current and direct current via adjustment of a duty cycle parameter.

18. A closed loop brain stimulation system, comprising:
means for reading electrophysiological signals from the brain;
means for reading other biometric signals;
means for stimulating the brain; and
a control algorithm that dynamically adjusts a mixing process affecting brain stimulation to minimize a reference utility function, including a cumulative measure of the difference between the current and desired brain states, and current and desired biometric states.

* * * * *